United States Patent
Mendes et al.

(10) Patent No.: US 10,662,152 B2
(45) Date of Patent: May 26, 2020

(54) CRYSTALLINE PHARMACEUTICAL CO-CRYSTALS OF GLYCOPYRRONIUM BROMIDE WITH LACTOSE

(71) Applicant: Hovione Scientia Limited, Cork (IE)

(72) Inventors: Zita Mendes, Lisbon (PT); Tiago Fonseca, Loures (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 16/307,383

(22) PCT Filed: Jun. 8, 2017

(86) PCT No.: PCT/GB2017/051664
§ 371 (c)(1),
(2) Date: Dec. 5, 2018

(87) PCT Pub. No.: WO2017/212273
PCT Pub. Date: Dec. 14, 2017

(65) Prior Publication Data
US 2019/0256463 A1    Aug. 22, 2019

(30) Foreign Application Priority Data
Jun. 8, 2016    (PT) ........................................ 109445

(51) Int. Cl.
| | |
|---|---|
| *A61P 13/06* | (2006.01) |
| *A61P 11/06* | (2006.01) |
| *A61P 11/00* | (2006.01) |
| *C07D 207/12* | (2006.01) |
| *C07H 3/04* | (2006.01) |

(52) U.S. Cl.
CPC ............ *C07D 207/12* (2013.01); *A61P 11/06* (2018.01); *C07H 3/04* (2013.01); *C07B 2200/13* (2013.01)

(58) Field of Classification Search
CPC A61P 13/06; A61P 11/06; A61P 29/00; A61P 11/00; C07H 3/04; C07D 207/12
See application file for complete search history.

(56) References Cited

U.S. PATENT DOCUMENTS

| | | |
|---|---|---|
| 4,899,739 A | 2/1990 | Konishi |
| 5,122,383 A | 6/1992 | Heiber et al. |
| 5,403,588 A | 4/1995 | Santa Ana, Jr. |
| 5,460,820 A | 10/1995 | Ebert et al. |
| 5,919,760 A | 7/1999 | Simon |
| 5,976,499 A | 11/1999 | Rubenstein et al. |
| 6,214,792 B1 | 4/2001 | Simon |
| 9,006,462 B2 | 4/2015 | Statler et al. |
| 2008/0227988 A1 | 9/2008 | Baxter et al. |
| 2010/0276329 A1 | 11/2010 | Johnston et al. |
| 2011/0146678 A1 | 6/2011 | Ruecroft et al. |
| 2014/0228330 A1 | 8/2014 | Ruecroft et al. |

FOREIGN PATENT DOCUMENTS

| | | |
|---|---|---|
| AU | 2013100007 A4 | 3/2013 |
| PT | 109445 | 6/2016 |
| WO | 2006092617 A1 | 9/2006 |
| WO | 2015036799 A1 | 3/2015 |
| WO | 2016001445 A1 | 1/2016 |
| WO | 2017212273 A1 | 12/2017 |

OTHER PUBLICATIONS

Glycopyrronium_bromide_Wikipedia, 2019, https://en.wikipedia.org/wiki/Glycopyrronium_bromide.*
Foreign communication from a related application—Search Report of Portuguese Patent Application No. 109445, dated Dec. 13, 2016, in Portuguese language, 5 pages.
Tscheng, Dorothy Z., "Sialorrhea—Therapeutic Drug Options," The Annals of Pharmacotherapy, Nov. 2002, pp. 1785-1790, vol. 36.
Foreign communication from a priority application—International Search Report and Written Opinion, PCT/GB2017/051664, dated Aug. 23, 2017, 23 pages.
Morissette, Sherry L., et al., "High-throughput crystallization: polymorphs, salts, co-crystals and solvates of pharmaceutical solids," Advanced Drug Delivery Reviews, 2004, pp. 275-300, vol. 56, Elsevier B.V.
Caira, Mino R., "Crystalline polymorphism of organic compounds," Topics in Current Chemistry, 1998, pp. 163-208, vol. 198, Springer Verlag Berlin Heidelberg.
Florence, Alastair J., "Polymorph screening in pharmaceutical development—European Pharmaceutical Review," European Pharmaceutical Review, Aug. 19, 2010, https://www.europeanpharmaceuticalreview.com/article/3659/polymorph-screening-in-pharmaceutical-development/, 15 pages.
Foreign communication from a priority application—Second Written Opinion, PCT/GB2017/051664, May 14, 2018, 10 pages.
Foreign communication from a priority application—International Preliminary Report on Patentability, PCT/GB2017/051664, dated Aug. 21, 2018, 19 pages.
Lee, Eun Hee, "A practical guide to pharmaceutical polymorph screening & selection," Asian Journal of Pharmaceutical Sciences, 2014, pp. 163-175, vol. 9, Elsevier B. V.

* cited by examiner

*Primary Examiner* — Sun Jae Yoo
(74) *Attorney, Agent, or Firm* — Conley Rose, P.C.; Rodney B. Carroll

(57) ABSTRACT

The present invention provides co-crystals of glycopyrronium bromide with lactose. The glycopyrronium bromide and lactose in the novel co-crystals are present in a stoichiometric ratio of from about 1:2 to 2:1. These are characterized by XRD and DSC. Processes for preparing the novel co-crystals are also provided. The co-crystals are also disclosed for use as a medicament, in particular, for treatment of respiratory complaints, such as chronic pulmonary obstructive disease (COPD), bronchitis and asthma. Pharmaceutical compositions comprising the co-crystals as active ingredient are also presented.

28 Claims, 2 Drawing Sheets

CRYSTALLINE PHARMACEUTICAL CO-CRYSTALS OF GLYCOPYRRONIUM BROMIDE WITH LACTOSE

CROSS REFERENCE TO RELATED APPLICATIONS

This application is a filing under 35 U.S.C. 371 of International Application No. PCT/GB2017/051664 filed Jun. 8, 2017, entitled "Crystalline Pharmaceutical Co-Crystals of Glycopyrronium Bromide with Lactose" which claims priority to Portuguese Patent Application No. 109445 filed Jun. 8, 2016, which applications are incorporated by reference herein in their entirety.

FIELD OF INVENTION

The present invention relates to co-crystals of glycopyrronium bromide and lactose, a process for preparing the co-crystals and to their use as a medicament, in particular, for treatment of respiratory complaints, such as chronic pulmonary obstructive disease (COPD), bronchitis and asthma. The invention also relates to a pharmaceutical composition comprising co-crystals of glycopyrronium bromide as active ingredient.

BACKGROUND TO THE INVENTION

Glycopyrronium bromide (also known as Glycopyrrolate bromide) is an antagonist of muscarinic receptor and used in the treatment of urinary incontinence (U.S. Pat. Nos. 6,214,792 and 5,919,760), sialorrhea (Tscheng, Z. Ann. Pharmacother, 2002), hyperhidrosis (US 20100276329), overactive bladder and for pre-surgery treatment. It is also an anticholinergic bronchodilator and used in the treatment of asthma and chronic obstructive pulmonary disease (COPD). Antimuscarinic bronchodilators are generally considered to be more effective for COPD than for asthma.

Glycopyrrolate is a quaternary ammonium cation and was previously available as a bromine salt (U.S. Pat. No. 5,919,760), as an acetate salt (U.S. Pat. No. 5,976,499), as a tosylate salt (U.S. Pat. No. 9,006,462), as an oxalate salt (U.S. Pat. No. 5,403,588), as hydrogen sulfate salt (U.S. Pat. No. 5,460,820), or benzoate salt (U.S. Pat. No. 4,899,739), or as edisylate salt (U.S. Pat. No. 5,122,383). Glycopyrronium bromide has a short half-life of 0.6 to 1.2 hours.

Since pharmaceutical compositions require that the active pharmaceutical substance (API) has to be stable both chemically and physically, a number of studies to provide more suitable new forms of the API were done.

The use of co-crystals is one possibility to improve bioavailability, and besides bioavailability several other properties can also be improved such as, dissolution rate, physical stability, mechanical proprieties, hygroscopicity, chemical stability, flowability and purification process ability.

Co-crystallization is a method of formation of mainly hydrogen bonds between an active pharmaceutical ingredient (API) molecule and a co-former, thus the API regardless of the presence of acidic, basic, or ionisable groups could potentially be co-crystallized.

A co-crystal consists of a crystalline material composed of at least two components that are solids at room temperature, preferably from about 15° C. to 25° C. Co-crystals are not necessarily binary compounds, ternary and quaternary co-crystals are also known.

A pharmaceutical co-crystal is simply a co-crystal in which at least one of the molecular components is an active pharmaceutical ingredient (API) in conjunction with another molecule termed as 'co-former' that is another API or other substance appearing on the GRAS (generally regarded as safe) status FDA list or those that have been demonstrated to be non-toxic.

Unlike salts, co-crystals do not rely on ionic interactions and therefore co-crystals can be made for forming non-ionisable drugs.

Co-crystals are new solid state forms that have new solid state proprieties. Co-crystallization can improve physiochemical proprieties like solubility, dissolution rate, chemical stability and melting point.

Glycopyrronium bromide is a long-acting muscarinic receptor antagonists (LAMAs) recently approved for the treatment of chronic obstructive pulmonary disease (COPD).

We have now appreciated that there is a need for a new crystalline form of glycopyrronium bromide which has enhanced pharmaceutical properties such as mechanical behaviour, solubility, dissolution rate, stability, drug solubility, and bioavailability.

SUMMARY OF THE INVENTION

The present inventors have now discovered a novel co-crystal of glycopyrronium bromide comprising glycopyrronium bromide and lactose, which meets, or substantially meets, the above needs. The novel pharmaceutical co-crystals of glycopyrronium bromide and lactose could provide enhanced pharmaceutical properties such as improved drug solubility and stability. An improvement in solubility of glycopyrronium bromide could be particularly advantageous for use in pharmaceutical formulations.

Accordingly, the present invention provides a co-crystal of glycopyrronium bromide comprising glycopyrronium bromide and lactose. Preferably, the lactose used in the present invention is selected from monohydrate lactose, anhydrous lactose or amorphous lactose. Preferably, the lactose is a crystalline lactose monohydrate.

In the novel co-crystal of the present invention, the glycopyrronium bromide and lactose are present preferably in a stoichiometric ratio of from about 1:2 to 2:1.

In the novel co-crystal of the present invention, the glycopyrronium bromide and lactose are present preferably in a stoichiometric ratio of about 1:1. This co-crystal of glycopyrronium bromide with lactose in a stoichiometric ratio of 1:1 is characterized by a single endothermic event at about 172° C. determined by DSC and by an X-Ray powder diffraction pattern having characteristic 2theta values at: 5.50; 9.12; 9.78; 10.84; 12.48; 13.7; 14.28; 14.38; 15.80; 16.18; 16.90; 18.16; 18.62; 19.36; 19.40; 19.54; 20.06; 21.06; 21.56; 21.92; 22.72; 23.38; 24.34; 24.64; 25.14; 25.76; 26.20; 27.02; 27.34; 28.52; 29.50; 29.98; 30.76; 32.52; 33.28; 34.64; 36.10; 37.06; 38.08; 39.18; 42.66 43.26; 45.38; ±0.2° 2θ.

In the novel co-crystal of the present invention, the glycopyrronium bromide and lactose are present preferably in a stoichiometric ratio of about 1:2. This co-crystal of glycopyrronium bromide with lactose in a stoichiometric ratio of 1:2 is characterized by a single endothermic event at about 172° C. determined by DSC and by an X-Ray powder diffraction pattern having characteristic 2theta values at: 5.44; 10.76; 12.48; 14.34; 15.76; 16.10; 16.48; 16.84; 18.56; 19.28; 19.98; 21.48; 21.88; 22.66; 23.36; 24.16; 24.28; 24.60; 25.08; 25.14; 25.72; 26.18; 26.94; 27.36; 28.48;

29.46; 29.94; 30.24; 30.72; 31.70; 32.12; 32.76; 33.24; 33.54; 34.12; 34.60; 35.36; 36.18; 37.06; 38.00; 38.24; 39.12; 40.24; 40.76; 41.36; 42.00; 42.58; 43.24; 43.94; 44.82; 45.36; 46.24; 46.70; 47.76; ±0.2° 2θ.

In the novel co-crystal of the present invention, the glycopyrronium bromide and lactose are present preferably in a stoichiometric ratio of about 2:1. This co-crystal of glycopyrronium bromide with lactose in a stoichiometric ratio of 2:1 is characterized by a single endothermic event at about 172° C. determined by DSC and by an X-Ray powder diffraction pattern having characteristic 2theta values at: 5.58; 10.92; 12.1; 12.76; 14.44; 14.48; 15.92; 16.28; 15.92; 16.62; 17.32; 18.22; 18.68; 19.4; 19.82; 20.22; 21.1; 21.62; 21.64; 22.08; 23.02; 23.42; 23.96; 24.44; 24.72; 25.32; 25.86; 26.34; 27.08; 27.46; 27.64; 28.62; 30.08; 30.38; 30.86; 31.28; 31.68; 31.92; 32.58; 32.90; 34.30; 34.74; 35.14; 35.50; 35.86; 36.44; 37.16; 37.80; 38.42; 38.74; ±0.2° 2θ.

The present invention also provides a co-crystal of glycopyrronium bromide and lactose for use as a medicament, preferably for use in the treatment of chronic pulmonary obstructive disease (COPD), bronchitis, asthma or hyperhidrosis.

The present invention also provides a pharmaceutical formulation comprising the novel co-crystals of glycopyrronium bromide and lactose of the present invention.

The present invention also provides a pharmaceutical formulation comprising co-crystals of glycopyrronium bromide and lactose and its use in the treatment of chronic pulmonary obstructive disease (COPD), bronchitis, asthma or hyperhidrosis.

The present invention also provides a process for producing co-crystals of glycopyrronium bromide and lactose. The process comprises:
(a) mixing glycopyrronium bromide and lactose in a solvent to form a reaction mixture;
(b) heating the reaction mixture to form a solution;
(c) adding an anti-solvent to the reaction mixture;
(d) cooling the reaction mixture, suitably under stirring to obtain a precipitate;
(e) filtering the precipitate; and
(f) drying the precipitate to obtain co-crystals of glycopyrronium bromide and lactose.

Alternatively, after cooling the reaction mixture in step d), the precipitate is spray dried.

In step (a) the glycopyrronium bromide and lactose are mixed preferably in a relative molar ratio in the range of from 0.5 to 2.2. Preferably, glycopyrronium bromide and lactose are mixed in a relative molar ratio in the range of from 1.0 to 2.2. Preferably, glycopyrronium bromide and lactose are mixed in a relative molar ratio in the range of from 0.5 to 1.8.

In step a) the glycopyrronium bromide and lactose is dissolved in a solvent preferably at a temperature of from about 40° C. to about 55° C., preferably from about 50° C. to about 55° C.

In step c) the anti-solvent is added to the reaction mixture preferably under stirring dropwise and maintained at a temperature of from 50° C. to 55° C. The reaction mixture is then cooled down in step d) preferably to a temperature of from about 20° C. to about 25° C., and kept at this temperature under stirring for 3 hours.

Preferably, after step e) the product is washed with a solvent such as ethyl acetate or methyl ethyl ketone (MEK). In step f) the product is preferably dried under vacuum, preferably at a temperature of from about 35° C. to about 40° C.

If the product is spray dried instead of filtering then post drying may not be necessary.

The dried co-crystals of glycopyrronium bromide and lactose from step f) may be further micronized by any known methods. The micronized co-crystals of glycopyrronium bromide and lactose have a particle size, preferably in the range of from about 2 microns to 5 microns.

Preferably, the lactose used in the process of the present invention is selected from: monohydrate lactose, anhydrous lactose or amorphous lactose. Preferably, the lactose is a crystalline lactose monohydrate.

Suitable solvent used in the process of the present invention includes, but not limited to, dimethylsulfoxide (DMSO), dimethylformamide (DMF), dimethylacetamide (DMA) and mixtures of one or more thereof.

Suitable anti-solvent used in the process of the present invention includes, but not limited to, aprotic solvent, ketones, esters, ethers and mixtures thereof. Examples of anti-solvent also includes, but not limited to acetonitrile, ethyl acetate, acetone and mixtures thereof. Preferably, the anti-solvent is ethyl acetate or methyl ethyl ketone (MEK).

DETAILED DESCRIPTION OF THE INVENTION

Figure 1:
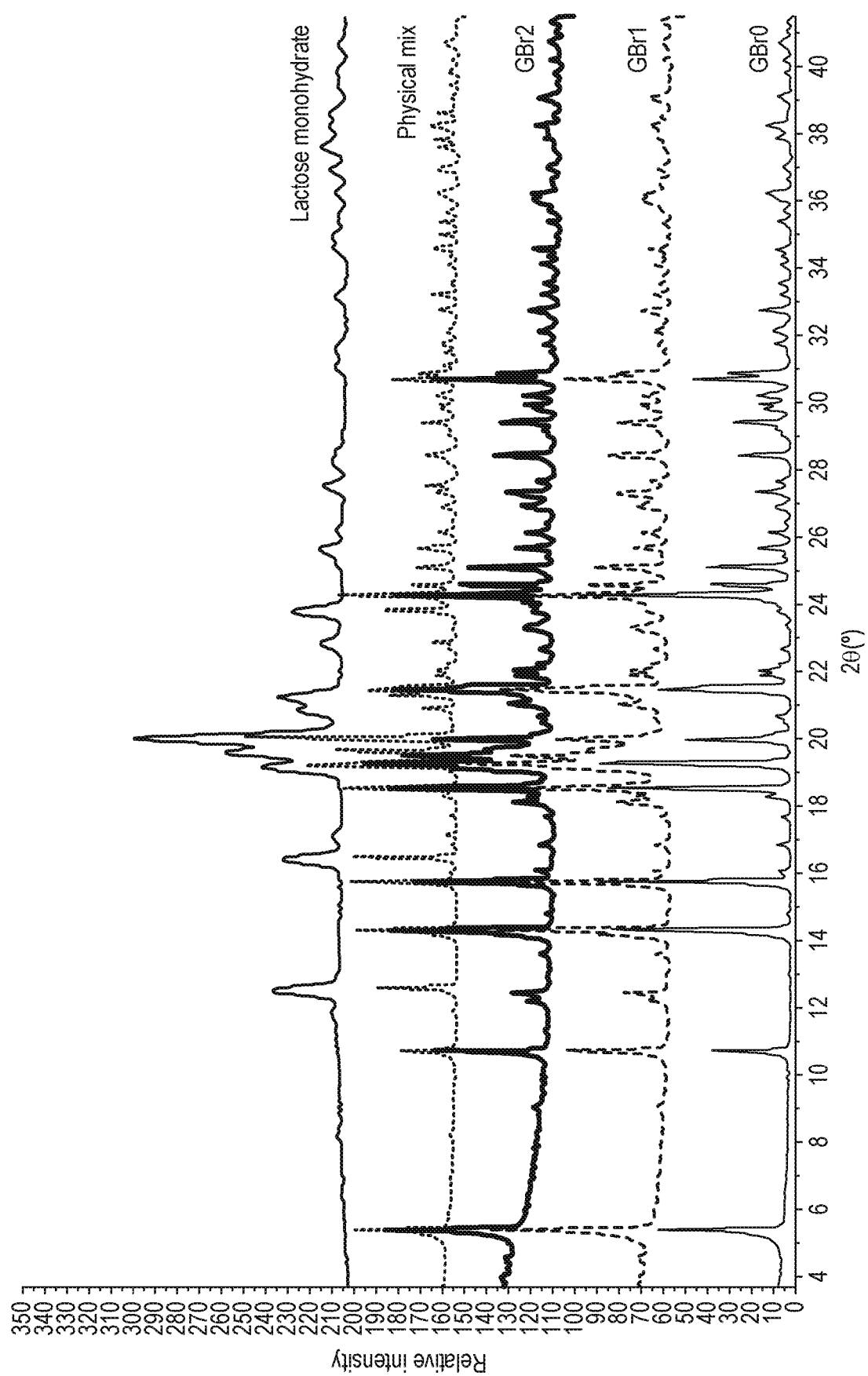
FIG. 1 shows HR-XRD powder pattern of: glycopyrrolate bromide ("GBr0"), essential pure co-crystals of glycopyrrolate bromide and lactose ("GBr1" and "GBr2"), a physical mixture of glycopyrrolate bromide and lactose monohydrate ("physical mix"), and lactose monohydrate ("lactose monohydrate").

The present invention describes the production of a crystal modification of glycopyrronium bromide that can be obtained in the form of a co-crystal with lactose.

The novel co-crystal of glycopyrronium bromide and lactose of the present invention has several advantages including, but not limited to, increase in dissolution rate without compromising the thermodynamic stability, and improved properties in relation to physical stability and bioavailability.

The present invention also describes a pharmaceutical formulation comprising the novel co-crystal of glycopyrronium bromide and lactose.

Co-crystals are being studied intensively primarily due to the potential for improved pharmaceutical properties, including bioavailability, dissolution rate, hygroscopicity, physical stability, purification processability, compressibility, flowability and shelf-life.

In the case of designing co-crystals of marketed drugs, clinical trials program will be significantly shorter and less risky than those of New Chemical Entities (NCEs) since co-crystals do not involve structural modification of the parent molecules.

Co-crystals are solids that are crystalline materials composed of two or more molecules in the same crystal lattice where each component is defined as either an atom, ion, or molecule and do not involve structural modification of the parent molecule. In contrast to salts, the intermolecular interactions are not ionic, but weak forces like hydrogen bonding, π stacking and Van der Waals forces.

Due to the higher complexity of their crystal structure, co-crystals are also less prone to suffer polymorphic transformations. API in co-crystals will not form solvates, hydrates during crystallization or storage.

The European Medicines Agency defines co-crystals as: "co-crystals are crystalline structures made up of two or more components in a definitive stoichiometric ratio where the arrangement in the crystal lattice is not based on ionic bonds".

Co-crystals of glycopyrronium bromide and lactose of the present invention can be prepared by various methods including, but not limited to, anti-solvent addition, microfluidization technology, high pressure homogenization (HPH), and spray congealing.

Co-crystals consist of multiple components in given stoichiometric ratio, where different molecular species interact by hydrogen bonding and by non-hydrogen bonding.

Co-crystals of glycopyrronium bromide and lactose of the present invention, have various ratios of glycopyrronium bromide and lactose. Preferably, the co-crystals of the present invention have a stoichiometric ratio in the range of from 1:2 to 2:1. The stoichiometry ratio refers to the ratio of molecules in the unit cell of the co-crystals. The stoichiometry ratio can be determined by known analytical technique. In the present invention, the stoichiometric ratio is calculated based on the amounts of actives used in the preparation of the co-crystals and analysis of the final product indicates that no free lactose is detected.

Method 1—Anti-Solvent Addition

Co-crystals of glycopyrronium bromide and lactose of the present invention may be obtained by:
(a) Mixing glycopyrronium bromide and lactose, preferably in a relative molar ratio, in the range of from 0.5 to 2.2, preferably in the range of from 1.0 to 2.2 or from 0.5 to 1.8, in a solvent to form a reaction mixture. The solvent is preferably selected from dimethylsulfoxide (DMSO), dimethylformamide (DMF), dimethylacetamide (DMA) or mixtures of one or more thereof.
(b) Heating the reaction mixture until a solution is obtained. Preferably, the reaction mixture is heated to a temperature of from about 40° C. to about 55° C., more preferably about 50° C. to about 55° C. to form a solution.
(c) Adding slowly to the reaction mixture, under stirring, an anti-solvent preferably an aprotic solvent. Suitable anti-solvents also includes, but not limited to, ketones, esters, ethers acetonitrile, ethyl acetate, acetone, methyl ethyl ketone (MEK) or mixtures of one or more and mixtures thereof.
(d) Cooling the reaction mixture under stirring.
(e) Filtering the product or spray drying the product; and
(f) Suitably drying under vacuum after filtering the product to obtain co-crystals of glycopyrronium bromide and lactose. If the product is spray dried then it may not be necessary to further dry the product.

In step (c) above, the anti-solvent may be added dropwise to the reaction mixture and the reaction mixture is kept at a temperature of from 50° C. to 55° C. to obtain a suspension.

In step (d) above, the reaction mixture may be cooled to a temperature of from about 20° C. to about 25° C. and the reaction mixture is kept at the temperature range of from about 20° C. to about 25° C. under stirring for 3 hours. After filtering, the product obtained in step (e) may be washed using a solvent preferably ethyl acetate or methyl ethyl ketone (MEK). In step d) above, the product may be dried under vacuum at a temperature of from about 35° C. to about 40° C. The lactose used in the process according to the present invention can be crystalline monohydrate lactose, anhydrous lactose or amorphous lactose, preferably crystalline lactose monohydrate.

The co-crystals obtained by the process of the present invention were analyzed by X-Ray powder diffraction (XRPD), and differential scanning calorimetry (DSC). The analysis showed that a new crystalline form, a co-crystal of glycopyrronium bromide and lactose is formed.

For XRPD, data collection was carried out at room temperature using monochromatic CuKα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.50≤2θ≤41.5° for the second) with an exposure time of 45 s for each frame. No background subtraction or curve smoothing was applied to the XRPD patterns.

For the present invention, melting properties were obtained from DSC thermograms, recorded with a heat flux DSC822e instructment (Mettler-Toledo GmbH, Switzerland). The DSC822e was calibrated for temperature and enthalpy with a small piece of indium (m.p.=156.6° C.; δHf=28.45 J/g). Samples (circa 2 mg) were sealed in standard 40 μl aluminium pans, pin-holed and heated in the DSC from 25° C. to 300° C., at a heating rate of 10° C./min. Dry $N_2$ gas, at a flow rate of 50 mL/min was used to purge the DSC equipment during measurement.

For the present invention, mass loss due to solvent or water loss from the crystals was determined by TGA/SDTA. Monitoring the sample weight, during heating in a TGA/SDTA851e instrument (Mettler-Toledo GmbH, Switzerland), resulted in a weight vs. temperature curve. The TGA/SDTA851e was calibrated for temperature with indium and aluminium. Samples were weighed into 100 μl aluminium crucibles (Mettler Toledo) and sealed. The lids were pin-holed right before the measurement and the crucibles heated in the TGA from 25 to 300° C. at a heating rate of 10° C. min$^{-1}$. Dry $N_2$ gas was used for purging.

The analysis indicated that co-crystals of glycopyrronium bromide and lactose with a stoichiometric ratio of 1:1 has a single endothermic event at about 172° C. determined by DSC and a characteristic diffraction peaks presented below:

| 2theta | I/I$_0$ |
| --- | --- |
| 5.50 | 64 |
| 9.12 | 3 |
| 9.78 | 3 |
| 10.84 | 66 |
| 12.48 | 5 |
| 13.7 | 4 |
| 14.28 | 10 |
| 14.38 | 10 |
| 15.80 | 7 |
| 16.18 | 15 |
| 16.90 | 4 |
| 18.16 | 11 |
| 18.62 | 13 |
| 19.36 | 18 |
| 19.40 | 18 |
| 19.54 | 17 |
| 20.06 | 10 |
| 21.06 | 10 |
| 21.56 | 100 |
| 21.92 | 8 |
| 22.72 | 5 |
| 23.38 | 8 |
| 24.34 | 9 |
| 24.64 | 11 |

-continued

| 2theta | I/I₀ |
|---|---|
| 25.14 | 7 |
| 25.76 | 6 |
| 26.20 | 7 |
| 27.02 | 20 |
| 27.34 | 10 |
| 28.52 | 11 |
| 29.50 | 10 |
| 29.98 | 6 |
| 30.76 | 9 |
| 32.52 | 7 |
| 33.28 | 5 |
| 34.64 | 9 |
| 36.10 | 6 |
| 37.06 | 5 |
| 38.08 | 8 |
| 39.18 | 5 |
| 42.66 | 5 |
| 43.26 | 6 |
| 45.38 | 6 |

The analysis also indicated that characteristic diffraction peaks of co-crystals of glycopyrronium bromide and lactose with a stoichiometric ratio of 1:2 may comprise one or more peaks presented below, and has a single endothermic event at about 172° C. determined by DSC:

| 2theta | I/I₀ |
|---|---|
| 5.58 | 44 |
| 10.92 | 53 |
| 12.1 | 11 |
| 12.76 | 32 |
| 14.44 | 19 |
| 14.48 | 19 |
| 15.92 | 16 |
| 16.28 | 18 |
| 15.92 | 16 |
| 16.62 | 25 |
| 17.32 | 10 |
| 18.22 | 14 |
| 18.68 | 20 |
| 19.4 | 48 |
| 19.82 | 40 |
| 20.22 | 76 |
| 21.1 | 22 |
| 21.62 | 100 |
| 21.64 | 99 |
| 22.08 | 16 |
| 23.02 | 16 |
| 23.42 | 13 |
| 23.96 | 26 |
| 24.44 | 22 |
| 24.72 | 20 |
| 25.32 | 16 |
| 25.86 | 21 |
| 26.34 | 15 |
| 27.08 | 26 |
| 27.46 | 16 |
| 27.64 | 16 |
| 28.62 | 21 |
| 30.08 | 13 |
| 30.38 | 11 |
| 30.86 | 21 |
| 31.28 | 12 |
| 31.68 | 11 |
| 31.92 | 11 |
| 32.58 | 10 |
| 32.90 | 11 |
| 34.30 | 14 |
| 34.74 | 20 |
| 35.14 | 14 |
| 35.50 | 10 |
| 35.86 | 11 |
| 36.44 | 19 |

-continued

| 2theta | I/I₀ |
|---|---|
| 37.16 | 19 |
| 37.80 | 16 |
| 38.42 | 20 |
| 38.74 | 13 |

The analysis also indicated that characteristic diffraction peaks of co-crystals of glycopyrronium bromide and lactose with a stoichiometric ratio of 2:1 may comprise one or more peaks presented below, and has a single endothermic event at about 172° C. determined by DSC:

| 2theta | I/I₀ |
|---|---|
| 5.44 | 50 |
| 10.76 | 55 |
| 12.48 | 9 |
| 14.34 | 35 |
| 15.76 | 27 |
| 16.10 | 18 |
| 16.48 | 9 |
| 16.84 | 9 |
| 18.56 | 34 |
| 19.28 | 48 |
| 19.98 | 36 |
| 21.48 | 100 |
| 21.88 | 21 |
| 22.66 | 11 |
| 23.36 | 14 |
| 24.16 | 23 |
| 24.28 | 34 |
| 24.60 | 28 |
| 25.08 | 20 |
| 25.14 | 21 |
| 25.72 | 17 |
| 26.18 | 15 |
| 26.94 | 25 |
| 27.36 | 18 |
| 28.48 | 24 |
| 29.46 | 23 |
| 29.94 | 16 |
| 30.24 | 13 |
| 30.72 | 31 |
| 31.70 | 10 |
| 32.12 | 12 |
| 32.76 | 13 |
| 33.24 | 12 |
| 33.54 | 10 |
| 34.12 | 12 |
| 34.60 | 18 |
| 35.36 | 9 |
| 36.18 | 14 |
| 37.06 | 11 |
| 38.00 | 13 |
| 38.24 | 13 |
| 39.12 | 11 |
| 40.24 | 9 |
| 40.76 | 11 |
| 41.36 | 9 |
| 42.00 | 10 |
| 42.58 | 10 |
| 43.24 | 13 |
| 43.94 | 10 |
| 44.82 | 9 |
| 45.36 | 13 |
| 46.24 | 10 |
| 46.70 | 9 |
| 47.76 | 10 |

Method 2—Co-Crystallization Using Co-Precipitation by Micro-Fluidization or Micro-Reaction Co-crystals of glycopyrronium bromide and lactose of the present invention may be obtained by using microreactor or microstructured reactor or microchannel reactor. A wide range of microreactors and microfluidizer are known in the art. Any known microreactor or microstructured reactor or microchannel reactor may be used in this method.

In the present invention, a microfluidizer processor (Microfluidics, Model MRT CR5) comprising a chamber with 75 μm diameter reaction channels followed by an auxiliary processing module with 200 μm diameter reaction channels was used.

The method comprises the following steps:
1. Dissolving the API (glycopyrronium bromide) and lactose in an appropriate solvent and placing the solution in a first inlet reservoir. The solvent is preferably selected from dimethylsulfoxide (DMSO), dimethylformamide (DMF), dimethylacetamide (DMA) or mixtures of one or more thereof.
2. Placing an anti-solvent in a second inlet reservoir. Preferably, the anti-solvent is selected from aprotic solvent, ketones, esters, ethers, acetone, acetonitrile, ethyl acetate or methyl ethyl ketone (MEK) and mixtures thereof.
3. Both the solution from step (1) and the anti-solvent from step (2) are pressurized in a combined stream via one or more intensifier pumps to the micro-reactor. The intensifier pump is preferably set to impose a pressure of 20 kPsi. A ratio of 1:2 of solvent and anti-solvent is maintained preferably by using a peristaltic pump which is set to impose the desired ratio.
4. Both solutions interact within the micro-reactor at a nano-scale level to form a suspension of particles by co-precipitation to form a co-crystal of glycopyrronium bromide and lactose.

Method 3—Co-Crystallization Method Via Particle Size Reduction Through Wet Milling Co-crystals of glycopyrronium bromide and lactose of the present invention may be obtained by using microreactor or microstructured reactor or microchannel reactor. Any known microreactor or microstructured reactor or microchannel reactor may be used in this method.

In the present invention, a microfluidizer processor (Microfluidics, Model MRT CR5) comprising a chamber with 75 μm diameter reaction channels followed by an auxiliary processing module with 200 μm diameter reaction channels was used.

Co-crystals of glycopyrronium bromide and lactose of the present invention may be obtained by:
1. Suspending the API (glycopyrronium bromide) and lactose in an appropriate anti-solvent and placing the suspension in an inlet reservoir. Preferably, the anti-solvent is selected from aprotic solvent, ketones, esters, ethers acetone, acetonitrile ethyl acetate, methyl ethyl ketone (MEK), and mixtures thereof
2. The suspension is pressurized via one or more intensifier pumps to the microchannel(s)
3. The suspension returns to the inlet reservoir being re-pressurized via one or more intensifier pumps to the micro-channel(s). The intensifier pump is preferably set to impose a pressure of 20 kPsi. A ratio of 1:2 of solvent and anti-solvent is maintained preferably by using a peristaltic pump which is set to impose the desired ratio.
4. The number of cycles through the microchannel(s) is defined according to the final target co-crystal purity, which may be determined by the skilled person.

Method 4—Spray Congealing (SC)

Co-crystals of glycopyrronium bromide and lactose of the present invention may be obtained by the Spray Congealing process described in WO2015036799, which is incorporated by reference in its entirety, comprising the following steps:

a) feeding a molten mixture of glycopyrronium bromide (a first substance) and lactose (a second substance) which are able to form co-crystals to an atomizer;
b) atomizing the molten mixture to droplets;
c) solidifying the droplets to particles; and
d) collecting the particles of co-crystals of glycopyrronium bromide and lactose.

Preferably, the co-crystals of glycopyrronium bromide and lactose obtained by the processes of the present invention are micronized.

The co-crystal according to the invention may be obtained in finely divided form using methods known in the prior art. Known methods of micronizing active substances, such as the air jet mill or the conical screen mill techniques may be used to micronize the co-crystals of glycopyrronium bromide and lactose of the present invention for use in a pharmaceutical composition.

For example, for delivery of pharmaceutical co-crystal of glycopyrronium bromide and lactose by inhalation the particle size may be in the range of from about 2 microns to 5 microns.

The lactose used above mentioned processes can be crystalline monohydrate, anhydrous or amorphous, preferably crystalline lactose monohydrate.

The co-crystals of glycopyrronium bromide and lactose of the present invention can be formulated in a pharmaceutical composition comprising the co-crystals and optionally one or more pharmaceutically acceptable excipients and/or surfactants. Suitable pharmaceutically acceptable excipients include carriers, diluents, wetting agents, emulsifying agents, binders, coatings, fillers, glidants, lubricants, disintegrants, preservatives, surfactants, pH buffering substances and the like known in the art may be used in the formulation.

The pharmaceutical compositions comprising the co-crystals as active ingredient can be used as a medicament, in particular, for treating respiratory complaints, such as chronic pulmonary obstructive disease (COPD), bronchitis and asthma.

The present invention further provides a method for the treatment in a mammal, such as a human, for treating respiratory, inflammatory or obstructive airway disease such as COPD and asthma, which method comprises administration of a therapeutically effective amount of a pharmaceutical composition comprising co-crystal of glycopyrronium bromide and lactose according to the present invention. The method of treatment may be characterized in that co-crystal of glycopyrronium bromide and lactose is administered in therapeutically effective amounts to the patient.

The pharmaceutical compositions may be prepared by admixing co-crystal of glycopyrronium bromide and lactose of the present invention and one or more pharmaceutically acceptable excipients.

The dosage and mode of administration can be decided by the expert of the art, based on the common general knowledge.

The pharmaceutical compositions may be formulated to be delivered by any suitable route, including oral, intravenous, parenteral, inhalation, intranasal, topical, subcutaneous, or intramuscular. Suitable dosage forms include, not limited to tablets, capsules, powders, sustained release formulations, ointments, gels, creams, suppositories, eye drops, transdermal patches, syrups, solutions, suspensions, aerosols, solutions for nebulizers, nasal sprays, etc.

The pharmaceutical compositions of the present invention may be administered by any suitable method used for delivery of drugs to the respiratory tract. The composition of the present invention may thus be administered using metered dose inhalers (MDI), dry powder inhalers (DPI), nebulisers, nasal sprays, nasal drops, insufflation powders, sprays and spray patches.

In a preferred embodiment, the pharmaceutical composition of the present invention is suitable for administration by inhalation or intranasal routes, such as an aerosol solution or suspension, as a dry powder for inhalation, or in a nasal spray. The composition for inhalation comprises co-crystal of glycopyrronium bromide and lactose having particle size. Preferably, the particle size of co-crystal glycopyrronium bromide and lactose can be in the range of from about 2 microns to about 5 microns.

The present invention further provides a method for the treatment in a mammal, such as a human, for treating hyperhidrosis.

EXAMPLES

The following examples are intended to illustrate the invention, without limiting it in any way.

Example 1—Preparation of Co-Crystals Glycopyrronium Bromide and Lactose

Glycopyrronium bromide (2.0 g; 5.0 mmol) and lactose monohydrate (1.98 g; 5.49 mmol) were dissolved in dimethylsulfoxide (DMSO) (10 ml) at a temperature of from 50° C. to 55° C. Then ethyl acetate (50 ml) was added dropwise maintaining the reaction mixture at a temperature of from 50° C. to 55° C.

A suspension is obtained and the reaction mixture is cooled down at a temperature of from 20° C. to 25° C. and kept at this temperature under stirring for 3 hours.

The product was filtered and washed with ethyl acetate and then dried under vacuum at a temperature of from 35° C. to 40° C., to yield 3.7 g of co-crystals of glycopyrronium bromide and lactose.

The product was analyzed using Differential Scanning Calorimetry (DSC). The XRPD result indicates that a new crystalline form, a co-crystal of glycopyrronium bromide with lactose is formed.

Figure 2:
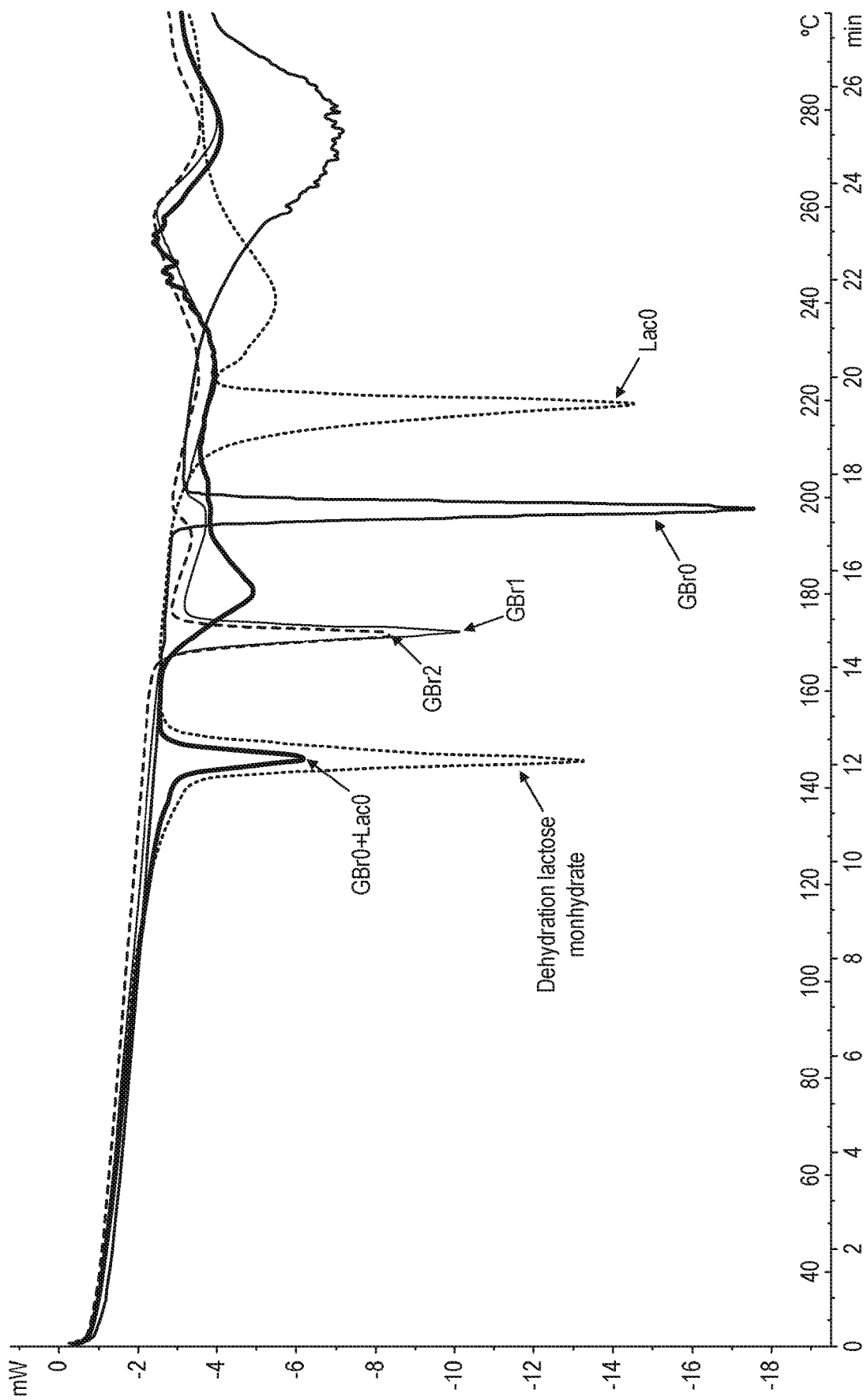
FIG. 2 shows DSC curves of glycopyrrolate bromide ("GBr0", purple), essential pure co-crystal of glycopyrrolate bromide and lactose ("GBr1" green), essential pure co-crystal of glycopyrrolate bromide and lactose ("GBr2" blue), and a physical mixture of glycopyrrolate bromide and lactose monohydrate ("GBr-Lac" red).

The XRPD and DSC characterization of the co-crystals is depicted as 'GBr1' in FIGS. 1 and 2.

Example 2—Preparation of Co-Crystals Glycopyrronium Bromide and Lactose

Glycopyrronium bromide (2.0 g; 5.0 mmol) and lactose monohydrate (1.98 g; 5.49 mmol) were dissolved in dimethylformamide (DMF) (10 ml) at a temperature of from 50° C. to 55° C. Then ethyl acetate (50 ml) was added dropwise maintaining the reaction mixture at a temperature of from 50° C. to 55° C.

A suspension is obtained and the reaction mixture is cooled down at 20°-25° C. and kept at this temperature under stirring for 3 hours.

The product is filtered and washed with ethyl acetate and then dried under vacuum at a temperature of from 35°-40° C. to yield 3.83 g of co-crystals of glycopyrronium bromide and lactose.

The product was analyzed using Differential Scanning Calorimetry (DSC). The XRPD result indicates that a new crystalline form, a co-crystal of glycopyrronium bromide with lactose is formed.

The XRPD and DSC characterization of the co-crystals is depicted as 'GBr2' in FIGS. 1 and 2.

Example 3—Preparation of Co-Crystals Glycopyrronium Bromide and Lactose

Glycopyrronium bromide (2.0 g; 5.0 mmol) and lactose monohydrate (1.98 g; 5.49 mmol) were dissolved in dimethylformamide (DMF) (40 ml) at a temperature of from 50° C. to 55° C. Then methyl ethyl ketone (MEK) (80 ml) was added dropwise maintaining the reaction mixture at a temperature of from 50° C. to 55° C.

A suspension is obtained and the reaction mixture is cooled down at 20°-25° C. and kept at this temperature under stirring for 3 hours.

The product is filtered, washed with methyl ethyl ketone (MEK) and then dried under vacuum at a temperature of from 35° C.-40° C. to yield 3.06 g of co-crystals of glycopyrronium bromide and lactose.

The product was analysed using Differential scanning calorimetry (DSC). The XRPD result indicates that a new crystalline form, a co-crystal of glycopyrronium bromide with lactose is formed.

Example 4—Preparation of Co-Crystals Glycopyrronium Bromide and Lactose

Glycopyrronium bromide (1.0 g; 2.5 mmol) and lactose monohydrate (1.8 g; 5.0 mmol) were dissolved in dimethylsulphoxide (DMSO) (15 ml) at a temperature of from 50° C. to 55° C. Then ethyl acetate (60 ml) was added dropwise maintaining the reaction mixture at a temperature of from 50° C. to 55° C.

A suspension is obtained and the reaction mixture is cooled down at temperature of from 20° C. to 25° C. and kept at this temperature under stirring for 3 hours.

The product is filtered, washed with ethyl acetate and then dried under vacuum at a temperature of from 25° C.-30° C. to yield 2.5 g of co-crystals of glycopyrronium bromide and lactose.

The product was analyzed using Differential Scanning Calorimetry (DSC). The XRPD result indicates that a new crystalline form, a co-crystal of glycopyrronium bromide with lactose is formed.

Example 5—Preparation of Co-Crystals Glycopyrronium Bromide and Lactose

Glycopyrronium bromide (1.0 g; 2.5 mmol) and lactose monohydrate (0.5 g; 1.38 mmol) were dissolved in dimethylsulphoxide (DMSO) (10 ml) at a temperature of from 50° C. to 55° C. Then ethyl acetate (40 ml) was added dropwise maintaining the reaction mixture at a temperature of from 50° C. to 55° C.

A suspension is obtained and the reaction mixture is cooled down at a temperature of from 20° C. to 25° C. and kept at this temperature under stirring for 3 hours.

The product is filtered, washed with ethyl acetate and then dried under vacuum at a temperature of from 25° to 30° C. to yield 0.88 g of co-crystals of glycopyrronium bromide and lactose.

The product was analyzed using Differential scanning calorimetry (DSC). The XRPD result indicates that a new crystalline form, a co-crystal of glycopyrronium bromide with lactose is formed.

The invention claimed is:

1. A co-crystal of glycopyrronium bromide comprising glycopyrronium bromide and lactose, wherein the glycopyrronium bromide and lactose are present in a stoichiometric ratio of from about 1:2 to 2:1.

2. The co-crystal according to claim 1, wherein the lactose is selected from monohydrate lactose, anhydrous lactose or amorphous lactose.

3. The co-crystal according to claim 1, wherein the lactose is a crystalline lactose monohydrate.

4. The co-crystal according to claim 1, wherein the stoichiometric ratio of glycopyrronium bromide and lactose in the co-crystal is 1:1.

5. The co-crystal according to claim 1, wherein the stoichiometric ratio of glycopyrronium bromide and lactose in the co-crystal is 1:2.

6. The co-crystal according to claim 1, wherein the stoichiometric ratio of glycopyrronium bromide and lactose in the co-crystal is 2:1.

7. The co-crystal according to claim 1, characterized by X-Ray spectrum with characteristic 2theta values at: 5.50; 9.12; 9.78; 10.84; 12.48; 1.3.7; 14.28; 14.38; 15.80; 1.6.18; 16.90; 18.16; 18.62; 19.36; 19.40; 19.54; 20.06; 21.06; 21.56; 21.92; 22.72; 23.38; 24.34; 24.64; 25.14; 25.76; 2620; 27.02; 27.34; 28.52; 29.50; 29.98; 30.76; 32.52; 33.28; 34.64; 36.10; 37.06; 38.08; 39.18; 42.66 43.26; and 45.38; ±0.2° 2θ.

8. The co-crystal according to claim 1, characterized by X-Ray spectrum with characteristic 2theta values at: 5.58; 10.92; 12.1; 12.76; 1.4.44; 14.48; 15.92; 16.28; 15.92; 16.62; 17.32; 18.22; 18.68; 19.4; 1.9.82; 20.22; 21.1; 21.62; 21.64; 22.08; 23.02; 23.42; 23.96; 24.44; 24.72; 25.32; 25.86; 26.34; 27.08; 27.46; 27.64; 28.62; 30.08; 30.38; 30.86; 31.28; 31.68; 31.92; 32.58; 32.90; 3430; 34.74; 3514; 35.50; 35.86; 36.44; 37.16; 37.80; 38.42; 38.74; ±0.2° 2θ.

9. The co crystal according to claim 1, characterized by X-Ray spectrum with characteristic 2theta values at: 5.44; 10.76; 12.48; 14.34; 15.76; 16.10; 16.48; 16.84; 18.56; 19.28; 19.98; 21.48; 21.88; 22.66; 23.36; 24.16; 24.28; 24.60; 25.08; 25.14; 25.72; 26.18; 26.94; 27.36; 28.48; 29.46; 29.94; 30.24; 30.72; 31.70; 32.12; 32.76; 33.24; 33.54; 34.12; 34.60; 35.36; 36.18; 37.06; 38.00; 38.24; 39.12; 40.24; 40.76; 41.36; 42.00; 42.58; 43.24; 43.94; 44.82; 45.36; 46.24; 46.70; 47.76; ±0.2° 2θ.

10. The co-crystal according to claim 1, characterized by a singe endothermic event at about 172° C. determined by DSC.

11. The co-crystal according to claim 1, wherein the co-crystal is in a micronized form.

12. The co-crystal according to claim 11, wherein the micronized co-crystal has a particle size in the range of about 2 microns to about 5 microns.

13. A method comprising administering a medicament comprising the co-crystal according to claim 1 to a subject in need thereof for the treatment of chronic pulmonary obstructive disease (COPD), bronchitis, asthma or hyperhidrosis.

14. A process for producing a co-crystal of glycopyrronium bromide comprising glycopyrronium bromide and lactose present in a stoichiometric ratio of from about 1:2 to 2:1, the process comprising the steps of:
(a) mixing glycopyrronium bromide and lactose in a solvent to form a reaction mixture;

(b) heating the reaction mixture to obtain a solution;
(c) adding an anti-solvent to the reaction mixture;
(d) cooling the reaction mixture, under stirring;
(e) filtering or spray drying the product obtained after cooling; and
(f) drying the product if required to obtain co-crystals of glycopyrronium bromide and lactose.

15. The process according to claim 14 wherein in step a) the glycopyrronium bromide and lactose are dissolved in a relative molar ratio of from 0.5 to 2.2.

16. The process according to claim 14, wherein in step f) the product is dried under vacuum at a temperature of from about 35° C. to about 40° C.

17. The process according to claim 14, wherein the product in step e) is washed using a solvent such as ethyl acetate or methyl ethyl ketone (MEK) or mixture thereof.

18. The process according to claim 14, wherein the lactose is selected from monohydrate lactose, anhydrous lactose or amorphous lactose.

19. The process according to claim 14, wherein the solvent is selected from dimethylsulfoxide (DMSO), dimethylformamide (DMF), dimethylacetamide (DMA) or mixtures of one or more thereof.

20. The process according to claim 14, wherein the anti-solvent is selected from aprotic solvent, ketones, esters, ethers, acetonitrile, acetone ethyl acetate or methyl ethyl ketone (MEK) or mixtures of one or more thereof.

21. The process according to claim 14, wherein the co-crystals of glycopyrronium bromide and lactose from step f) is micronized.

22. The process according to claim 21, wherein the micronized co-crystals of glycopyrronium bromide and lactose have a particle size of about 2 microns to about 5 microns.

23. The process according to claim 14, wherein in step h) the reaction mixture is heated to a temperature of from 50° C. to 55° C. to form a solution.

24. The process according to claim 14, wherein in step d) the reaction mixture is cooled to a temperature of from about 2.0° C. to about 25° C., and the reaction mixture is kept at this temperature under stirring for about 3 hours to obtain a precipitate.

25. A pharmaceutical formulation comprising co-crystals of glycopyrronium bromide and lactose according to claim 1 and one or more pharmaceutically acceptable excipients.

26. A method comprising administering a pharmaceutical composition comprising the co-crystals glycopyrronium bromide and lactose according to claim 1 to a subject in need thereof for the treatment of chronic pulmonary obstructive disease (COPD), bronchitis or asthma.

27. The process according to claim 14, wherein the lactose is a crystalline lactose monohydrate.

28. The pharmaceutical formulation according to claim 25, wherein the pharmaceutically acceptable excipient comprises one or more surfactants.

* * * * *

UNITED STATES PATENT AND TRADEMARK OFFICE
CERTIFICATE OF CORRECTION

PATENT NO. : 10,662,152 B2
APPLICATION NO. : 16/307383
DATED : May 26, 2020
INVENTOR(S) : Zita Mendes et al.

It is certified that error appears in the above-identified patent and that said Letters Patent is hereby corrected as shown below:

In the Claims
Claim 7, Column 13, Line 17, replace "1.3.7" with --13.7--.
Claim 7, Column 13, Line 17, replace "1.6.18" with --16.18--.
Claim 7, Column 13, Line 20, replace "2620" with --26.20--.
Claim 8, Column 13, Line 25, replace "1.4.44" with --14.44--.
Claim 8, Column 13, Line 26, replace "1.9.82" with --19.82--.
Claim 8, Column 13, Line 29, replace "3430" with --34.30--.
Claim 8, Column 13, Line 29, replace "3514" with --35.14--.
Claim 23, Column 14, Line 32, replace "step f)" and replace with --step b)--.

Signed and Sealed this
Eleventh Day of August, 2020

Andrei Iancu
*Director of the United States Patent and Trademark Office*